United States Patent

Repolles Moliner et al.

Patent Number: 5,432,159
Date of Patent: Jul. 11, 1995

[54] N-(α-SUBSTITUTED-PYRIDINYL)CARBONYL DIPEPTIDE ANTIHYPERTENSIVE AGENTS

[75] Inventors: Jose Repolles Moliner; Francisco Pubill Coy; Lydia Cabeza Llorente; Carlos Malet Falco, all of Barcelona, Spain

[73] Assignee: Lacer S.A., Barcelona, Spain

[21] Appl. No.: 938,248

[22] PCT Filed: Feb. 26, 1992

[86] PCT No.: PCT/EP92/00400
§ 371 Date: Oct. 27, 1992
§ 102(e) Date: Oct. 27, 1992

[87] PCT Pub. No.: WO92/15608
PCT Pub. Date: Sep. 17, 1992

[30] Foreign Application Priority Data

Feb. 27, 1991 [EP] European Pat. Off. ......... 91102950

[51] Int. Cl.6 .......................................... A61J 38/06
[52] U.S. Cl. ........................................ 514/18; 514/19; 530/331; 548/535; 546/281
[58] Field of Search ................. 514/19, 18; 530/331; 548/535; 546/281

[56] References Cited

FOREIGN PATENT DOCUMENTS 0080283  6/1983  European Pat. Off. .
3332633  4/1985  Germany .
2045771  11/1980  United Kingdom .

OTHER PUBLICATIONS

Biological Abstracts, vol. 90, No. 11, 1990, AN 126221, "Synthesis of N-(2-mercaptopyridyl-3-formyl-)-N-alkylglycine and the corresponding disulfides".

Primary Examiner—Jill Warden
Assistant Examiner—David Lukton
Attorney, Agent, or Firm—Oblon, Spivak, McClelland, Maier, & Neustadt

[57] ABSTRACT

Dipeptide derivatives are taught which are of general formula (I)

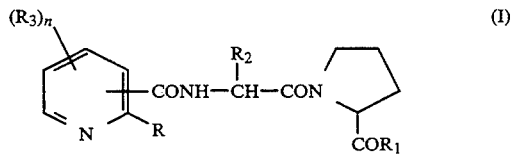

including tautomeric forms thereof, wherein:

n is 0 or an integer of from 1 to 3;

R is OH, SH, COOH, $NH_2$, halogen, $OR_4$, $SR_4$, $COOR_4$, $NHR_4$ or $N(R_4)_2$, $R_4$ being selected from lower alkyl, optionally substituted, aryl and acyl groups;

$R_1$ represents OH, lower alkoxy, optionally substituted, aryl lower alkoxy, aryloxy or disubstituted amino groups;

$R_2$ is selected from lower alkyl and amino lower alkyl groups;

$R_3$ represents halogen, $NO_2$, lower alkyl, halo lower alkyl, aryl lower alkyl or aryl;

and pharmaceutically acceptable salts thereof.

These derivatives are useful, among others, in the treatment of hypertension.

7 Claims, No Drawings

N-(α-SUBSTITUTED-PYRIDINYL)CARBONYL DIPEPTIDE ANTIHYPERTENSIVE AGENTS

The present invention relates to new N-(α-substituted-pyridinyl)carbonyl-dipeptides which act as inhibitors of the angiotensin-converting enzyme. These novel compounds may be formulated, along with pharmaceutically acceptable carriers, into pharmaceutical compositions useful in the treatment of hypertension and other cardiovascular disorders whose pathophysiology involves the reninangiotensin-aldosterone system.

During the seventies, the pharmacotherapy of arterial hypertension underwent a substantial advance, due to the development of agents showing a direct action on reninangiotensin and kallikrein-kinin systems and, especially, the synthesis of the first compounds effectively inhibiting the enzymatic conversion of the decapeptide angiotensin I to the potent vasopressor angiotensin II, i.e., acting as inhibitors of the angiotensin-converting enzyme (ACE). This physiologically important enzyme also degrades the vasodilating peptide bradykinin. Several ACE inhibitors have proved capable, in experimental animals and humans, of inhibiting the pressor effects of intravenously administered angiotensin I, and have shown antihypertensive activity in animal models and hypertensive patients. Their suitability for the treatment of congestive heart failure also has convincingly been demonstrated.

U.S. Pat. No.4,105,776 discloses N-acyl derivatives of α-amino acids which are effective ACE inhibitors and, as such, useful in the treatment of hypertension. The compounds specifically concerned are mercapto derivatives of N-acyl-L-proline, including the most representative member of the series, i.e., D-3-mercapto-2-methylpropanoyl-L-proline or captopril, the first orally active ACE inhibitor antihypertensive agent made available worldwide.

Another important breakthrough in this field, but with a totally different approach, is represented by compounds disclosed in EP-A-12401, which are carboxyalkyl-dipeptide derivatives and whose more representative members are enalaprilat, enalapril and lisinopril.

A better understanding of the ACE structure and of the respective essential structural requirements for potential inhibitors, as well as an interest in providing novel compounds with different potency, kinetics and/or toxicity profiles, have led to a continuous development of new classes of ACE inhibitors. From several studies of structure-activity relationships, it has been concluded that an effective inhibition of the enzyme can only be achieved with a molecule that shows at least three clearly distinguishable regions or parts, as represented by the following general structure:

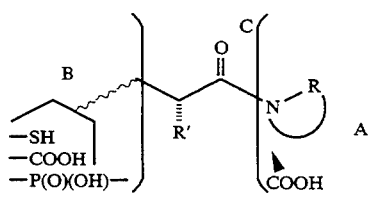

Region A usually has a carboxyl group in the α-position, which group strongly binds to a cationic site of the enzyme structure. In several studies it has been found that L-proline is the best substructure for this region or part, although its pyrrolidine ring can also be present in a modified form.

Region B has to contain a functional group with a specific ability to bind the $Zn^{++}$ cation located in the "active site" of the enzyme. This zinc-binding group, usually an acidic one, can be a mercapto group (captopril and analogues) or a carboxyl group (enalaprilat, lisinopril and analogues) as well as any precursor group which can give rise to an active group by metabolic conversion. Examples of ACE inhibitors with precursor groups are the acylthio derivatives alacepril and pivalopril and the carboxylic esters enalapril and perindopril. Some classes of inhibitors have other acidic groups in the B region, for example, —P(O)(OH)— or —P(O)(OH)O— in free or esterified form. In any case, all known zinc ligands are invariably linked to an alkyl group or, sometimes, to a cycloalkyl group, but never as part of an aromatic structure (M. J. Wyvratt, A. A. Patcherr, Medicinal Research Reviews 5, 483–531, 1985).

Region C acts as a bridge between the active sites of regions A and B and apparently has to satisfy definite stereochemical requirements, as the most active compounds show an L-amino acid derived unit (for example, an L-alanine or L-lysine unit) in the corresponding dipeptide structure. In the captopril-type group, the same stereochemistry must be present on C-2 of the 2-methylpropanoyl unit.

This simplified general model applies to almost all of the different structures of the known ACE inhibitors, special or additional requirements having to be satisfied within each particular chemical class. In this context, the best-known structure-activity relationships are certainly those elucidated in the mercapto acyl-amino acid (captopril group) and the carboxyalkyl-dipeptide (enalapril/lisinopril analogues) series. Although systematic variations have been carried out in each of the three structural parts, it is worth mentioning that, in both of said general series, the different attempts to find zinc-binding groups different from mercapto or carboxy have, usually, resulted in inactive compounds or at least a considerable loss of activity of the compounds concerned. Particularly, in the class of dipeptide derivatives, effective ACE inhibitors with N-substituted carboxamides or thioamides as zinc ligands have not been disclosed so far.

The present invention provides new dipeptide derivatives with ACE inhibiting activity and displaying, as fundamental and distinguishing feature, a substructure constituted by a pyridine ring having attached thereto a potentially zinc-binding functionality, specifically an α-substituent selected from, for example, OH, SH, $NH_2$ and COOH or functionally related or precursor groups thereof. This α-substituted pyridine substructure, linked through a carbonyl group to the terminal amino group of the dipeptide, is located in a part of the general structure which corresponds to region B discussed above. As region A, the L-proline substructure has been chosen, with an amino acid such as L-alanine in the bridging region C.

Because of said specific structural features, the dipeptide derivatives of the present invention cannot be included or categorized in any of the general classes or any of the particular chemical families disclosed to date in the field of ACE inhibitors.

Within the general dipeptide class, the compounds of the present invention are clearly different from the carboxyalkyl dipeptides, as they have an arylcarbonyl-dipeptide structure. Said structural arrangement is very unusual in the field of natural or synthetic ACE inhibitors. Moreover, (α-substituted-pyridinyl)carbonyl-dipeptides have not been disclosed or suggested in the prior art literature, as can be taken, for example, from the classical reviews on this subject by E. W. Petrillo and M. A. Ondetti (Medicinal Research Reviews 2, 1-41, 1982) and by M. J. Wyvratt and A. A. Patcherr (see above).

Furthermore, from a practical point of view, it is to be taken into account that the carboxyalkyl dipeptide inhibitors of the prior art have an asymmetric carbon (in the region B) in addition to the two asymmetric carbons of the dipeptide substructure, which renders their synthesis very complex and/or results in low yields, due to the necessary optical resolution of the crude products. Since the compounds of the present invention do not have this additional asymmetric carbon atom, they can readily be obtained in good yields by introducing the pyridinyl carbonyl moiety into the desired dipeptide through the terminal $NH_2$ group thereof.

In its broadest aspect, the present invention relates to new dipeptide derivatives of general formula (I):

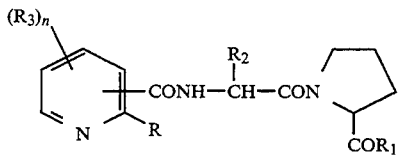

(I)

including tautomeric forms thereof, wherein:

n is 0 or an integer of from 1 to 3;

R is OH, SH, COOH, $NH_2$, halogen, $OR_4$, $SR_4$, $COOR_4$, $NHR_4$ or $N(R_4)_2$, $R_4$ being selected from lower alkyl, optionally substituted, aryl and acyl groups;

$R_1$ represents OH, lower alkoxy, optionally substituted, aryl lower alkoxy, aryloxy or disubstituted amino groups;

$R_2$ is selected from lower alkyl and amino lower alkyl groups;

$R_3$ represents halogen, $NO_2$, lower alkyl, halo lower alkyl, aryl lower alkyl or aryl;

and pharmaceutically acceptable salts thereof.

$R_3$ in formula (I) may occupy any free position of the pyridine ring.

Likewise, the substituted pyridine ring may be linked to the carbonyl-dipeptide substructure through the α, β or γ-positions of the pyridine ring, one of the α-positions being already occupied by the R group.

The pharmaceutically acceptable salts of compounds of formula (I), for instance when $R_1$ is OH and/or R is COOH, include those with alkali metals such as sodium or potassium or alkaline earth metals, such as calcium. They also include ammonium salts, for example, with ammonia, substituted amines or basic amino acids.

As is well-known in the field of nitrogen-containing heterocycles, pyridine derivatives α-substituted by hydroxy or mercapto groups are usually present in their tautomeric forms, i.e., as 2-pyridinones and 2-pyridinethiones, respectively, i.e., as particular types of cyclic carboxamides and thioamides. For this reason, it is to be understood that the compounds of general formula (I), wherein R is OH or SH, may also show this tautomerism, the respective amidic forms being usually predominant. Although a classical aromatic structure is shown in formula (I), this specific structural representation has been chosen only for the purpose of simplification, since thereby it is possible to include all the different functional groups R in a single general formula. Furthermore, this structural representation readily shows the relationships between some specific R groups, for instance, in the case of the different $OR_4$ groups and the (unsubstituted) OH group. It is known in pyridine chemistry that, for example, α-alkoxy-pyridines can be hydrolised to their α-hydroxy-pyridines and, hence, to the more favoured α-pyridinone tautomers.

Therefore, it should be evident that general formula (I) does not imply a specific preferred hydroxy- or mercapto tautomerism in case R is OH or SH. On the contrary, the predominant tautomeric forms in this latter case may be represented by general formula (Ia):

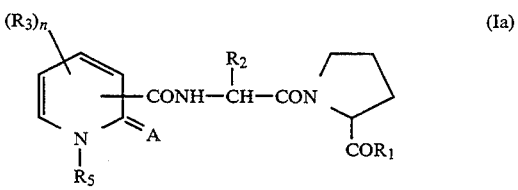

(Ia)

wherein A represents O or S, $R_1$, $R_2$ and $R_3$ are as defined above, and $R_5$ is hydrogen or lower alkyl.

In formula (Ia), only compounds for which $R_5$ is hydrogen are "true" tautomeric forms of compounds of formula (I), wherein R is OH or SH. Compounds of formula (Ia) wherein $R_5$ is lower alkyl, although also included in the present invention, in a strict sense are not tautomeric forms of compounds of formula (I) wherein R is $OR_4$ or $SR_4$, $R_4$ being said lower alkyl group.

Preferred dipeptide derivatives of the present invention are those wherein, in general formula (I) above, n is 0 or 1, particularly 0, and R, $R_1$, $R_2$ and $R_3$ are defined as follows:

R: OH, SH, COOH, Cl, $OR_4$, $SR_4$, $NHR_4$ or $COOR_4$, $R_4$ being selected from lower alkyl, aryl or acyl groups; even more preferred are: $OR_6$, $SR_6$, Cl, $NHR_7$ or $COOR_8$, wherein $R_6$ is hydrogen, lower alkyl or optionally substituted phenyl, particularly hydrogen, methyl, ethyl or phenyl; $R_7$ is acyl or optionally substituted phenyl, particularly acetyl or phenyl; and $R_8$ is hydrogen or lower alkyl, particularly hydrogen, methyl or ethyl.

$R_1$: OH or lower alkoxy, particularly OH, methoxy and ethoxy;

$R_2$: lower alkyl, particularly methyl;

$R_3$: $NO_2$ and/or halogen (particularly Br).

The terms "lower alkyl", "lower alkoxy" etc. as used herein and in the appended claims are meant to denote the following groups:

lower alkyl: linear or branched alkyl groups having 1 to 6, preferably 1 to 4, carbon atoms, such as methyl, ethyl, n-propyl, i-propyl and butyl; most preferably methyl and ethyl;

lower alkoxy: the lower alkyl groups as defined above attached to an oxygen atom, preferably $OCH_3$ and $OC_2H_5$;

halogen: F, Cl, Br and I, particularly Cl and Br;

aryl: preferably having 6 to 14, particularly 6 to 10, carbon atoms, such as phenyl and naphthyl, optionally substituted with one or more substituents selected from, for example, lower alkyl (such as methyl), lower alkoxy (such as methoxy), halogen (such as Cl and F) and $NO_2$;

acyl: (alkyl- and aryl-)carbonyl groups, preferably having a total of 1 to 10, particularly 2 to 7, carbon atoms, such as acetyl, propionyl, pivaloyl and benzoyl;

substituted lower alkyl: the above lower alkyl groups (particularly methyl and ethyl) substituted with one or more, preferably one or two, and particularly one, substituent selected from the above lower alkoxy groups (such as methoxy and ethoxy), halogen (particularly F and Cl), OH, acyloxy (wherein the acyl groups are defined as above) and di(lower alkyl)amino (lower alkyl being defined as above), specific examples of substituted lower alkyl groups being 1-acetoxy-ethyl (axetil), pivaloyloxymethyl (pivoxil) and dimethylaminoethyl;

halo lower alkyl: the above lower alkyl groups (particularly methyl and ethyl) substituted with one or more halogen atoms, preferably selected from F, Cl and Br, particularly F and Cl, such as $CF_3$, $CCl_3$, $CHCl_2$ and $CH_2Cl$;

aryl lower alkyl: the above aryl groups (particularly optionally substituted phenyl) attached to a lower alkyl group as defined above, such as benzyl and 1- and 2-phenethyl;

disubstituted amino: an $NH_2$ group, wherein both hydrogen atoms have been replaced by carbon-containing groups, particularly lower alkyl groups as defined above; specific examples thereof being dimethylamino and diethylamino.

The remaining terms can be deduced from the above definitions. For instance, "substituted lower alkoxy" means a substituted lower alkyl group as defined above attached to an oxygen atom.

When n in general formula (I) has the value of 1, the group $R_3$ is preferably located in a β-position of the pyridine ring, and particularly in the β-position opposed to the α-position occupied by the R group.

The compounds of general formula (I), as well as the subgroup of compounds which may also be represented by formula (Ia), show the two asymmetric centers of the dipeptide substructure and are, thus, capable of existing in several stereoisomeric forms. Although this invention embraces each of these individual stereoisomeric forms and any mixtures thereof, the preferred compounds are those wherein both asymmetric centers have the "S" configuration.

The compounds of formula (I) are inhibitors of the angiotensin converting enzyme and are useful as antihypertensive agents in meals (including humans). They can also be used in the treatment of congestive heart failure and other disorders pathophysiologically associated with the renin-angiotensin-aldosterone system.

Thus, a further aspect of the present invention is represented by pharmaceutical compositions comprising at least one compound of general formula (I) in combination with one or more pharmaceutically acceptable carriers or excipients and, optionally, adjuvants and/or complementary agents, etc. in solid or liquid form and preferably in unit dosage form. The compositions of this invention may, most suitably, be adapted for oral administration, although other routes of administration such as parenteral, rectal or by inhalation may be even more advantageous in certain instances. The pharmaceutical compositions of the present invention can be prepared in conventional manner, for example, by simple mixing of the ingredients of the desired composition. Suitable carriers or excipients are the conventional ones and well-known to the skilled person. Oral administration is best achieved with formulations in the form of tablets (coated or uncoated), capsules or liquids, such as solutions, syrups or suspensions. The oral solid form can be of the conventional type, i.e. of fast release, or with sustained release characteristics.

For the purpose of treating hypertension and/or possibly other disorders for which the biological activity of these novel compounds may be useful, dosage levels of the order of 2 to 1000 mg per patient per day, in single or multiple doses, are appropriate, although the individual dose level for each patient will depend on the activity of the specific compound used, the type and severeness of affliction as well as individual factors such as body weight and sex, and other factors usually known to those skilled in the art. For the treatment of hypertension, the dose will preferably range from 5 to 500 mg per patient per day.

The compounds of this invention can also be administered in combination with other pharmaceutically active compounds, for example, anti-hypertensive agents or other agents useful in cardiovascular therapy, such as diuretics or β-adrenergic blockers. Said other active compounds can also be incorporated in the pharmaceutical compositions of the present invention together with the novel compounds of general formula (I).

The compounds of general formula (I) can be prepared by one or more of the methods described below. It will be apparent to those skilled in the art that other synthetic approaches well-known in peptide chemistry can also be adopted.

The first method (method A) comprises the coupling of a carboxylic acid of formula (IIa) with a dipeptide of formula (III)

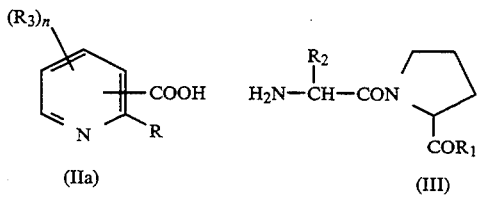

wherein R, $R_1$, $R_2$, $R_3$ and n are as defined above, but excluding COOH for R and OH for $R_1$, in the presence of, preferably, an equimolar amount of a suitable coupling agent, for, example, a carbodiimide and, particularly, N,N'-dicyclohexylcarbodiimide (DCC). Generally, the reaction is carried out in a suitable basic organic solvent and at room temperature.

The dipeptide of formula (III) is preferably employed in the form of an ester such as a lower alkyl ester. The free amino group may, optionally, be salified, for example, with hydrochloric acid. Examples of suitable basic organic solvents are pyridine and a mixture of a tertiary aliphatic amine (for example, triethylamine) with an inert, preferably halogenated, solvent (such as chloroform or methylene chloride). When starting from the preferred esterified dipeptide, the desired compound of formula (I) is obtained as monoester (in the L-proline substructure) in case R is a group different from $COOR_4$, or as diester, when a compound of formula (IIa) with R=$COOR_4$ ($R_4$=alkyl, aryl) is used.

It will be apparent that, when the starting dipeptide has an additional amino group, i.e., when $R_2$ is amino lower alkyl, said additional amino group must be present in protected form, for example, protected with a benzyloxycarbonyl group or any other group which is readily removable by standard methods known to the skilled person.

According to a variation of method A, one can employ substantially the same procedure but substitute an esterified amino acid of formula $H_2N-CH(R_2)-COR_1$ for the dipeptide of formula (III). The N-(α-substituted-pyridinyl)carbonyl-amino acid ester thus obtained may then be hydrolised, reacting the resulting free acid with an L-proline ester by the DCC reaction or any other method usually employed for the coupling of amino acids.

Specific compounds of formula (Ia) wherein $R_5$ is lower alkyl can also be obtained by method A or variations thereof. In this case, an appropriate 1-alkyl-1,α-dihydro-α-(oxo- or thioxo)-pyridinecarboxylic acid is used as starting material.

Compounds of general formula (I) may also be prepared by reacting an acyl halide of formula (IIb) with a dipeptide of formula (III) or, for example, its hydrochloride (method B):

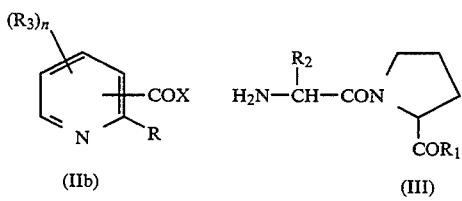

wherein X is halogen such as chloro, and R, $R_1$, $R_2$, $R_3$ and n are as defined above. When $R_1$ is different from OH, the reaction is preferably carried out in the presence of an organic base such as triethylamine, whereas an inorganic base such as alkali hydroxides or carbonates, or mixtures thereof, are employed when $R_1$ is OH.

When the starting dipeptide of formula (III) has a derived carboxyl group and an organic base is used (method B-a), the reaction is generally conducted in a suitable non-polar solvent, like chloroform, methylene chloride or dioxane. When said dipeptide has a free carboxyl group (method B-b), a biphasic system is advantageously employed. Said biphasic system usually comprises an aqueous solution of the inorganic base and a solution of the acyl halide in an appropriate organic solvent, such as acetonitrile, as the second phase.

When the starting compounds of formulae (IIa) or (IIb) have two vicinal COOH groups or groups derived therefrom, i.e., when R is COOH or $COOR_4$ and COOH or COX occupy the 3-position, methods A or B may result in the production of cyclic imides if the reaction conditions (temperature, time of reaction) are such that an intramolecular cyclisation of the reaction products is favoured. Mild reaction conditions, and especially low temperatures, are preferred in this case in order to minimize the appearance of cyclisation by-products.

As in the case of method A, when method B is applied to a dipeptide of formula (III) wherein $R_2$ is an amino lower alkyl group said additional amino group needs to be protected beforehand by an easily removable group.

Method B (a or b) can also be used for preparing a compound of formula (Ia) wherein $R_5$ is lower alkyl. In this case, the dipeptide of formula (III) is reacted with the corresponding 1-alkyl-1, α-dihydro-α-(oxo- or thioxo)-pyridine carbonyl halide.

The specific subgroup of N-(α-mercapto-pyridinyl)-carbonyldipeptides, i.e., compounds of formula (I) wherein R is SH (or A is S and $R_5$ is hydrogen in formula (Ia)) can also be obtained in high yields by method C, which method comprises the heating of a compound of formula (I) wherein R is halogen with sodium thiosulfate in a suitable hydroalcoholic medium such as mixtures of water and 1,2-propyleneglycol.

With any of the methods A to C described above, when the novel compounds of the invention are obtained as monoesters (in the proline rest) or as diesters (α-substituted in the pyridine ring by a carboxyl ester group), i.e., compounds of formula (I) in which only $COR_1$ or both $COR_1$ and R are carboxylic acid ester groups, said compounds can be converted to the respective free mono- or dicarboxylic acids by hydrolysis, for example, with an alkali hydroxide in a polar medium. Typical hydrolyric conditions include the use of potassium hydroxide dissolved in a lower aliphatic (for example $C_1$-$C_3$) alcohol, alone or in admixture with water. A preferred alcohol is ethanol.

The pyridinecarboxylic acids of formula (IIa), especially those with R=halogen, are commercially available or can be prepared by well-known synthetic procedures. The acid halides of formula (IIb) may easily be obtained by standard methods, starting from the corresponding acids of formula (IIa).

The starting dipeptides of formula (III) are also commercial products or may be synthesized by methods currently used in peptide chemistry.

Specific embodiments of the present invention are illustrated by the following non-limiting examples.

$^1$H-NMR and $^{13}$C-NMR spectra were recorded at 199.975 MHz and at 50.289 MHz, respectively, on a Varian XR-200 spectrometer. The chemical shifts are given as δ-values relative to tetramethyl silane, which was used as internal standard. Thin-layer-chromatographic analyses (TLC) were performed on precoated plates of Merck silica gel 60 $F_{254}$, and the spots were detected by UV irradiation. The following solvents were used in TLC:

A: Ethyl acetate
B: Ethyl acetate/acetone 3/1
C: Acetone
D: Absolute ethanol
E: Ethanol/acetic acid 3%
F: Ethanol/acetic acid 5% and are indicated in parenthesis in each case.

EXAMPLE 1

Synthesis of N-[(6-Chloro-2-pyridinyl)carbonyl]-L-alanyl-L-proline ethyl ester (Compound No. 1)

A solution of L-alanyl-L-proline ethyl ester hydrochloride (6 g, 0.024 mol) and triethylamine (7.4 ml) in anhydrous methylene chloride (120 ml) is cooled in an ice bath.

While stirring, a solution of 6-chloro-2-pyridinecarbonyl chloride (5.1 g, 0.029 mol) in anhydrous methylene chloride (30 ml) is added dropwise. Upon completion of the addition, the solution is stirred for 3 hours at room temperature and the reaction mixture is diluted with 400 ml of methylene chloride. The resulting solution is washed three times with 200 ml of 10% aqueous sodium bicarbonate and twice with 200 ml of water.

The organic layer is dried over anhydrous magnesium sulfate, and the solvent is distilled off under reduced pressure to give the title product as a colourless oil (yield 99%).

$^1$H-NMR (CDCl$_3$): 1.24 (t, J=7.2 Hz, 3H, CH$_3$ ethyl ester), 1.47 (d, J=6.8 Hz, 3H, CH$_3$ alanine), 2.10 (m, 4H, N—CH$_2$—CH$_2$—CH$_2$ proline), 3.70 (m, 2H, N—CH$_2$ proline), 4.15 (q, J=7.2 Hz, 2H, CH$_2$ ethyl ester), 4.50 (m, 1H, CH proline), 4.90 (m, 1H, CH alanine, converted to q, J=6.8 Hz, after shaking with D$_2$O), 7.40 (dd, J$_1$=7 Hz, J$_2$=1 Hz, 1H, ar), 7.75 (dd J$_1$=J$_2$=7 Hz, 1H, ar C-4), 8.02 (dd, J$_1$=7 Hz, J$_2$=1 Hz, 1H, ar), 8.50 (br d, 1H, NH, disappears after shaking with D$_2$O).

$^{13}$C-NMR (CDCl$_3$): 13.9 (CH$_3$ ethyl ester), 17.7 (CH$_3$ alanine), 24.8 (N—CH$_2$—CH$_2$ proline), 28.8 (N—CH$_2$—CH$_2$—CH$_2$ proline), 46.7 (CH alanine and N—CH$_2$ proline), 58.9 (CH proline), 61.1 (CH$_2$ ethyl ester), 120.9 (ar C-3), 127.2 (ar C-5), 139.9 (ar, C-4), 150.2 (ar), 150.4 (ar), 162.5 (CO), 171.0 (CO), 172.1 (CO). TLC (B): R$_f$=0.46.

Similarly, the following compounds are synthesized:

N-[(2-Chloro-3-pyridinyl)carbonyl]-L-alanyl-L-proline ethyl ester (Compound No. 2)

$^1$H-NMR (CDCl$_3$): 1.28 (t, J=7.2 Hz, 3H, CH$_3$ ethyl ester), 1.54 (d, J=6.8 Hz, 3H, CH$_3$ alanine) , 2.10 (m, 4H, N—CH$_2$—CH$_2$—CH$_2$ proline) , 3.73 (m, 2H, N—CH$_2$ proline) , 4.19 (q, J=7.2 Hz, 2H, CH$_2$ ethyl ester), 4.54 (m, 1H, CH proline), 4.96 (m, 1H, CH alanine). 7.34 (dd, J$_1$=7.7 Hz, J$_2$=4.8 Hz, 1H, ar C-5), 7.55 (br d, 1H, NH), 8.05 (dd J$_1$=7.7 Hz, J$_2$=2 Hz, 1H, ar C-4), 8.47 (dd, J$_1$=4.8 Hz, J$_2$=2 Hz, 1H, ar C-6). TLC(B): R$_f$=0.37.

N-[(2-Chloro-4-pyridinyl) carbonyl]-L-alanyl-L-proline ethyl ester (Compound No. 3)

$^1$H-NMR (CDCl$_3$): 1.27 (t, J=7.2 Hz, 3H, CH$_3$ ethyl ester), 1.50 (d, J=6.9 Hz, 3H, CH$_3$ alanine), 2.10 (m, 4H, N—CH$_2$—CH$_2$—CH$_2$ proline), 3.77 (m, 2H, N—CH$_2$ proline), 4.22 (q, J=7.2 Hz, 2H, CH$_2$ ethyl ester), 4.57 (m, 1H, CH proline), 4.91 (m, 1H, CH alanine), 7.51 (dd, J$_1$=5.1 Hz, J$_2$=1 Hz, 1H, ar C-5), 7.66 (d, J=1 Hz, 1H, ar C-3), 8.09 (d, J=7.2 Hz, 1H, NH), 8.43 (d, J=5.1 Hz, 1H, ar C-6). TLC(B): R$_f$=0.47.

N-[(6-Chloro-3-pyridinyl) carbonyl]-L-alanyl-L-proline ethyl ester (Compound No. 4)

$^1$H-NMR (CDCl$_3$): 1.27 (t, J=7.2 Hz, 3H, CH$_3$ ethyl ester), 1.48 (d, J=6.8 Hz, 3H, CH$_3$ alanine), 2.15 (m, 4H, N—CH$_2$—CH$_2$—CH$_2$ proline), 3.70 (m, 2H, N—CH$_2$ proline), 4.17 (q, J=7.2 Hz, 2H, CH$_2$ ethyl ester), 4.54 (m, 1H, CH proline), 4.94 (m, 1H, CH alanine), 7.32 (d, J=8.4 Hz, 1H, ar C-5), 8.03 (dd, J$_1$=8.4 Hz, J$_2$=2.4 Hz, 1H, ar C-4), 8.78 (d, J=2.4 Hz, 1H, ar C-2). TLC(B): R$_f$=0.46.

EXAMPLE 2

Synthesis of
N-[(1,2-Dihydro-2-thioxo-4-pyridinyl)carbonyl]-L-alanyl-L-proline ethyl ester (Compound No. 5)

To a solution of 4.5 g (0.013 mol) of N-[(2-Chloro-4-pyridinyl)carbonyl]-L-alanyl-L-proline ethyl ester (Compound No. 3) in 45 ml of a 10:1 mixture of 1,2-propyleneglycol:water, 15.2 g of sodium thiosulfate are added, and the mixture is heated under reflux for 15 hours. The resulting reaction mixture is diluted with 100 ml of water and extracted with four 100 ml portions of methylene chloride. The organic layer is washed three times with 100 ml of water, dried over anhydrous magnesium sulfate, and the solvent is distilled off at reduced pressure. The residue obtained is purified by crystallisation from a mixture of acetone:petroleum ether, to give the title product as a yellow solid (yield: 85%).

$^1$H-NMR (CDCl$_3$): 1.27 (t, J=7.2 Hz, 3H, CH$_3$ ethyl ester), 1.68 (d, J=7.0 Hz, 3H, CH$_3$ alanine), 2.10 (m, 4H, N—CH$_2$—CH$_2$—CH$_2$ proline), 3.75 (m, 2H, N—CH$_2$ proline), 4.28 (q, J=7.2 Hz, 2H, CH$_2$ ethyl ester), 4.55 (m, 1H, CH proline), 4.75 (m, 1H, CH alanine, converted to q, J=6.8 Hz, after shaking with D$_2$O), 6.78 (dd, J$_1$=6.6 Hz, J$_2$=1.6 Hz,. 1H, ar C-5), 7.31 (d, J=6.6 Hz, 1H, ar C-6), 7.88 (d, J=1.6 Hz, 1H, ar C-3), 8.70 (br d, 1H, amidic NH, disappears after shaking with D$_2$O).

$^{13}$C-NMR (CDCl$_3$): 13.9 (CH$_3$ ethyl ester), 15.5 (CH$_3$ alanine), 24.7 (N—CH$_2$—CH$_2$ proline), 28.7 (N—CH$_2$—CH$_2$—CH$_2$ proline), 46.8 (N—CH$_2$ proline), 48.1 (CH alanine), 59.2 (CH proline), 61.2 (CH$_2$ ethyl ester), 111.8 (ar C-5), 130.9 (ar C-3), 137.1 (ar C-6), 139.7 (ar, C-4), 165.0 (CO), 171.7 (CO), 172.9 (CO), 178.7 (CS). TLC(C): R$_f$=0.50

Similarly, the following compounds were synthesized:

N-[(1,2-Dihydro-2-thioxo-3-pyridinyl)carbonyl]-L-alanyl-L-proline ethyl ester (Compound No. 6)

$^1$H-NMR (CDCl$_3$): 1.21 (t, J=7.2 Hz, 3H, CH$_3$ ethyl ester), 1.54 (d, J=6.9 Hz, 3H, CH$_3$ alanine), 2.10 (m, 4H, N—CH$_2$—CH$_2$—CH$_2$ proline), 3.75 (m, 2H, N—CH$_2$ proline), 4.12 (q, J=7.2 Hz, 2H, CH$_2$ ethyl ester), 4.55 (m, 1H, CH proline), 4.85 (m, 1H, CH alanine), 6.72 (dd, J$_1$=6.1 Hz, J$_2$=7.6 Hz, 1H, ar C-5), 7.65 (dd J$_1$=6.1 Hz, J$_2$=1.7 Hz, 1H, ar C-4), 8.46 (dd, J$_1$=7.6 Hz, J$_2$=1.7 Hz, 1H, ar C-6), 11.15 (br d, 1H, NH). TLC(C): R$_f$=0.47

N-[(1,6-Dihydro-6-thioxo-3-pyridinyl)carbonyl]-L-alanyl-L-proline ethyl ester (Compound No. 7)

$^1$H-NMR (CDCl$_3$): 1.17 (t, J=7.2 Hz, 3H, CH$_3$ ethyl ester), 1.51 (d, J=7.0 Hz, 3H, CH$_3$ alanine), 2.10 (m, 4H, N—CH$_2$—CH$_2$—CH$_2$ proline), 3.72 (m, 2H, N—CH$_2$ proline), 4.13 (q, J=7.2 Hz, 2H, CH$_2$ ethyl ester), 4.50 (m, 1H, CH proline), 4.72 (m, 1H, CH alanine), 7.19 (d, J=9.0 Hz, 1H, ar C-5), 7.56 (dd, J$_1$=9.0 Hz, 1H, ar C-4), 7.83 (d, J=2 Hz, 1H, ar C-2), 8.27 (br d, 1H, NH). TLC(C): R$_f$=0.55

EXAMPLE 3

Synthesis of
N-[(2-Ethoxycarbonyl-6-pyridinyl)carbonyl]-L-alanyl-L-proline ethyl ester (Compound No. 8)

To a stirred solution of 4.31 g (0.022 mol) of 6-ethoxycarbonyl-2-pyridinecarboxylic acid in 100 ml of anhydrous pyridine, there are added 5.5 g (0.022 mol) of L-alanyl-L-proline ethyl ester hydrochloride and 4.6 g of N,N'-dicyclohexyl carbodiimide. Stirring is continued for 20 minutes at room temperature, and the bulky precipitate of dicyclohexyl urea is filtered and washed with acetone. The solvent from the filtrate and washings is distilled off under reduced pressure and the crude product obtained is purified by column chromatography over silica gel using chloroform:acetone (10:1) as eluant. The isolated solid is crystallized from an acetone/isopropyl ether/petroleum ether mixture, to give 4.27 g of the desired product as acicular crystals (yield: 53%).

$^1$H-NMR (CDCl$_3$): 1.28 (t, J=7.2 Hz, 3H, CH$_3$ aliphatic ester), 1.46 (t, 3H, J=7.2 Hz, CH$_3$ aromatic ester), 1.55 (d, J=6.8 Hz, 3H, CH$_3$ alanine), 2.15 (m, 4H, N—CH$_2$—CH$_2$—CH$_2$ proline), 3.75 (m, 2H, N—CH$_2$ proline), 4.21 (q, J=7.2 Hz, 2H, CH$_2$ aliphatic ester), 4.48 (q, J=7.2 Hz, 2H, CH$_2$ aromatic ester), 4.53 (m, 1H, CH proline), 5.00 (m, 1H, CH alanine, converted to q, J=6.8 Hz, after shaking with D$_2$O), 7.99 (dd, J$_1$=J$_2$=7.6 Hz, 1H, ar C-4), 8.22 (dd, J$_1$=7 Hz, J$_2$=1 Hz, 1H, ar), 8.33 (dd, J$_1$=7.6 Hz, J2=1 Hz, 1H, ar), 8.70 (br d, 1H, amidic NH, disappears after shaking with D$_2$O).

$^{13}$C-NMR (CDCl$_3$): 14.1 (CH$_3$ ethyl ester), 14.2 (CH$_3$ ethyl ester), 17.8 (CH$_3$ alanine), 24.9 (N—CH$_2$—CH$_2$ proline), 29.0 (N—CH$_2$—CH$_2$—CH$_2$ proline), 46.9 (CH alanine and N—CH$_2$ proline), 59.3 (CH proline), 61.3 (CH$_2$ ethyl ester), 62.4 (CH$_2$ ethyl ester), 125.5 (ar), 127.6 (ar), 138.7 (ar, C-4), 147.6 (ar), 150.1 (ar), 163.5 (CO), 165.0 (CO), 171.2 (CO), 172.4 (CO). TLC(B): R$_f$=0.63

Similarly, the following compounds are synthesized:

N-[(2-Methoxycarbonyl-5-pyridinyl)carbonyl]-L-alanyl-L-proline ethyl ester (Compound No. 9)

$^1$H-NMR (CDCl$_3$): 1.26 (t, J=7.2 Hz, 3H, CH$_3$ aliphatic ethyl ester), 1.51 (d, J=6.8 Hz, 3H, CH$_3$ alanine), 2.10 (m, 4H, N—CH$_2$—CH$_2$—CH$_2$ proline), 3.80 (m, 2H, N—CH$_2$ proline), 4.03 (s, 3H, CH$_3$ aromatic methyl ester), 4.17 (q, J=7.2 Hz, 2H, CH$_2$ ethyl ester), 4.55 (m, 1H, CH proline), 4.99 (m, 1H, CH alanine), 8.12 (d, J=8.4 Hz, 1H, ar C-3), 8.26 (dd, J$_1$=8.4 Hz, J$_2$=2.0 Hz, 1H, ar C-4), 8.43 (d, J=7.4 Hz, 1H, NH), 9.12 (d, J=2.0 Hz, 1H, ar C-6). TLC(B): R$_f$=0.36

N-[(2-Methoxycarbonyl-3-pyridinyl)carbonyl]-L-alanyl-L-proline ethyl ester (Compound No. 10)

$^1$H-NMR (CDCl$_3$): 1.23 (t, J=7.2 Hz, 3H, CH$_3$ ethyl ester), 1.50 (d, J=6.8 Hz, 3H, CH$_3$ alanine), 2.10 (m, 4H, N—CH$_2$—CH$_2$—CH$_2$ proline), 3.70 (m, 2H, N—CH$_2$ proline), 3.94 (s, 3H, CH$_3$ methyl ester), 4.15 (q, J=7.2 Hz, 2H, CH$_2$ ethyl ester), 4.50 (m, 1H, CH proline), 4.80 (m, 1H, CH alanine), 7.0 (br d, 1H, NH), 7.45 (dd, J$_1$=7.8 Hz, J$_2$=4.7 Hz, 1H, ar C-5), 7.84 (dd, J$_1$=7.8 Hz, J$_2$=1.7 Hz, 1H, ar, C-4), 8.70 (dd, J$_1$=4.7 Hz, J$_2$=1.7 Hz, 1H, ar, C-6). TLC(B): R$_f$=0.27

N-[(5-Bromo-1,2-dihydro-2-oxo-3-pyridinyl)carbonyl]-L-alanyl-L-proline ethyl ester (Compound No. 11)

$^1$H-NMR (CDCl$_3$): 1.28 (t, J=7.2 Hz, 3H, CH$_3$ ethyl ester), 1.53 (d, J=6.8 Hz, 3H, CH$_3$ alanine), 2.10 (m, 4H, N—CH$_2$—CH$_2$—CH$_2$ proline), 3.75 (m, 2H, N—CH$_2$ proline), 4.20 (q, J=7.2 Hz, 2H, CH$_2$ ethyl ester), 4.60 (m, 1H, CH proline), 4.88 (m, 1H, CH alanine), 7.71 (d, J=2.8 Hz, 1H, ar C-4), 8.48 (d, J=2.8 Hz, 1H, ar C-6), 10.10 (br d, 1H, amidic NH). TLC(D): R$_f$=0.76

N-[(1,2-Dihydro-2-oxo-4-pyridinyl)carbonyl]-L-alanyl-L-proline ethyl ester (Compound No. 12)

$^1$H-NMR (CDCl$_3$): 1.21 (t, J=7.2 Hz, 3H, CH$_3$ ethyl ester), 1.47 (d, J=7.0 Hz, 3H, CH$_3$ alanine), 2.10 (m, 4H, N—CH$_2$—CH$_2$—CH$_2$ proline), 3.75 (m, 2H, N—CH$_2$ proline), 4.12 (q, J=7.2 Hz, 2H, CH$_2$ ethyl ester), 4.50 (m, 1H, CH proline), 4.80 (m, 1H, CH alanine), 6.51 (dd, J$_1$=6.7 Hz, J$_2$=1.2 Hz, 1H, ar C-5), 6.97 (d, J=1.2 Hz, 1H, ar C-3), 7.25 (d, J=6.7 Hz, 1H, ar C-6), 8.46 (br d, 1H, amidic NH). TLC(D): R$_f$=0.49

N-[(1,6-Dihydro-6-oxo-2-pyridinyl)carbonyl]-L-alanyl-L-proline ethyl ester (Compound No. 13)

$^1$H-NMR (CDCl$_3$): 1.22 (t, J=7.2 Hz, 3H, CH$_3$ ethyl ester), 1.48 (d, J=6.8 Hz, 3H, CH$_3$ alanine), 2.10 (m, 4H, N—CH$_2$—CH$_2$—CH$_2$ proline), 3.57 (m, 2H, N—CH$_2$ proline), 4.17 (q, J=7.2 Hz, 2H, CH$_2$ ethyl ester), 4.48 (m, 1H, CH proline), 4.90 (m, 1H, CH alanine), 6.73 (dd, J$_1$=9.2 Hz, J$_2$=0.8 Hz, 1H, ar C-5), 6.91 (dd, J$_1$=7.0 Hz, J$_2$=1.0 Hz, 1H, ar C-3), 7.44 (dd, J$_1$=9.0 Hz, J$_2$=7.0 Hz, 1H, ar C-4), 8.46 (br d, 1H, amidic NH). TLC(C): R$_f$=0.43

N-[(1,6-Dihydro-6-oxo-3-pyridinyl)carbonyl]-L-alanyl-L-proline ethyl ester (Compound No. 14)

$^1$H-NMR (CDCl$_3$): 1.22 (t, J=7.0 Hz, 3H, CH$_3$ ethyl ester), 1.40 (d, J=7.0 Hz, 3H, CH$_3$ alanine), 2.10 (m, 4H, N—CH$_2$—CH$_2$—CH$_2$ proline), 3.75 (m, 2H, N—CH$_2$ proline), 4.10 (q, J=7.0 Hz, 2H, CH$_2$ ethyl ester), 4.50 (m, 1H, CH proline), 4.85 (m, 1H, CH alanine), 6.34 (d, J=9.0 Hz, 1H, ar C-5), 7.80 (d, J=8.8 Hz, 1H, ar C-4), 7.97 (s, 1H, ar C-2), 8.65 (d, J=6.8 Hz, amidic NH). TLC(D) R$_f$=0.50

N-[(2-Phenoxy-3-pyridinyl)carbonyl]-L-alanyl-L-proline ethyl ester (Compound No. 15)

$^1$H-NMR (CDCl$_3$): 1.15 (t, J=7.1 Hz, 3H, CH$_3$ ethyl ester), 1.30 (d, J=7.0 Hz, 3H, CH$_3$ alanine), 2.10 (m, 4H, N—CH$_2$—CH$_2$—CH$_2$ proline), 4.03 (m, 2H, N—CH$_2$ proline), 4.05 (q, J=7.1 Hz, 2H, CH$_2$ ethyl ester), 4.33 (m, 1H, CH proline), 4.80 (m, 1H, CH alanine), 7.21 (m, 5H, O-Ph), 7.42 (m, 2H, ar), 8.23 (m, 1H, ar), 8.78 (d, J=8.0 Hz, 1H, amidic NH): TLC (A): R$_f$=0.39

N-[(2-Phenylthio-3-pyridinyl)carbonyl]-L-alanyl-L-proline ethyl ester (Compound No. 16)

$^1$H-NMR (DMSO): 1.16 (t, J=7.2 Hz, 3H, CH$_3$ ethyl ester), 1.32 (d, J=7.0 Hz, 3H, CH$_3$ alanine), 1.96 (m, 4H, N—CH$_2$—CH$_2$—CH$_2$ proline), 3.69 (m, 2H, N—CH$_2$ proline), 4.06 (q, J=7.2 Hz, 2H, CH$_2$ ethyl ester), 4.35 (m, 1H, CH proline), 4.72 (m, 1H, CH alanine), 7.21 (dd, J$_1$=8.0 Hz, J$_2$=4.8 Hz, 1H, ar C-5), 7.40 (m, 5H, —S—Ph), 7.88 (dd, J$_1$=7.6 Hz, J$_2$=1.8 Hz, 1H, ar C-4), 8.33 (dd, J$_1$=4.8 Hz, J$_2$=1.8 Hz, 1H, ar C-6), 8.87 (d, J=8.0 Hz, 1H, amidic NH). TLC(A): R$_f$=0.33

N-[(2-Phenylamino-3-pyridinyl)carbonyl]-L-alanyl-L-proline ethyl ester (Compound No. 17)

$^1$H-NMR (DMSO): 1.14 (t, J=7.2 Hz, 3H, CH$_3$ ethyl ester), 1.19 (d, J=6.6 Hz, 3H, CH$_3$ alanine), 1.72 (m, 4H, N—CH$_2$—CH$_2$—CH$_2$ proline), 3.70 (m, 2H, N—CH$_2$ proline), 4.03 (q, J=7.2 Hz, 2H, CH$_2$ ethyl ester), 4.20 (m, 1H, CH proline), 4.56 (m, 1H, CH alanine), 7.22 (m, 5H, ar), 7.45 (dd, J$_1$=6.0 Hz, J$_2$=4.6 Hz, 1H, ar C-5), 7.60 (d, J=8 Hz, 1H, NH), 8.08 (m, 1H, ar), 8.47 (dd, J$_1$=4.8 Hz, J$_2$=1.4 Hz, 1H, ar C-6), 8.91 (s, 1H, amidic NH). TLC(A): R$_f$=0.22

N-[(1,2-Dihydro-5-nitro-2-oxo-3-pyridinyl)carbonyl]-L-alanyl-L-proline ethyl ester (Compound No. 18)

$^1$H-NMR (DMSO): 1.17 (t, J=7.1 Hz, 3H, CH$_3$ ethyl ester), 1.29 (d, J=7.0 Hz, 3H, CH$_3$ alanine), 2.10 (m, 4H, N—CH$_2$—CH$_2$—CH$_2$ proline), 3.60 (m, 2H, N—CH$_2$ proline), 4.12 (q, J=7.1 Hz, 2H, CH$_2$ ethyl ester), 4.32 (m, 1H, CH proline), 4.78 (m, 1H, Ch alanine), 8.77 (d, J=3.3 Hz, 1H, ar C-4), 8.89 (d, J=3.3 Hz, 1H, ar C-6), 10.01 (d, J=6.9 Hz, 1H, NH). TLC(D): R$_f$=0.74

N-[(1,2-Dihydro-1-methyl-2-oxo-3-pyridinyl)carbonyl]-L-alanyl-L-proline ethyl ester (Compound No. 19)

$^1$H-NMR (CDCl$_3$): 1.16 (t, J=7.0 Hz, 3H, CH$_3$ ethyl ester), 1.28 (d, J=6.8 Hz, 3H, CH$_3$ alanine), 2.10 (m, 4H, N—CH$_2$—CH$_2$—CH$_2$ proline), 3.45 (s, 3H, N—CH$_3$), 3.60 (m, 2H, N—CH$_2$ proline), 4.06 (q, J=7.2 Hz, 2H, CH$_2$ ethyl ester), 4.31 (m, 1H, CH proline), 4.76 (m, 1H, CH alanine), 6.48 (dd, J$_1$=J$_2$=7.0 Hz, 1H, ar C-5), 8.06 (dd, J$_1$=7.0 Hz, J$_2$=2.2 Hz, 1H, ar C-4), 8.29 (dd, J$_1$=7.0 Hz, J$_2$=2.2 Hz, 1H, ar C-6), 10.23 (br d, 1H, NH). TLC(D): R$_f$=0.51

N-[(2-Acetylamino-4-pyridinyl)carbonyl]-L-alanyl-L-proline ethyl ester (Compound No. 20)

$^1$H-NMR (d$_6$-DMSO): 1.17 (t, J=7.5 Hz, 3H, CH$_3$ ethyl ester), 1.33 (d, J=7 Hz, 3H, CH$_3$ alanine), 1.96 (m, 4H, N—CH$_2$—CH$_2$—CH$_2$ proline), 2.11 (s, 3H, CH$_3$ acetylamino), 3.67 (m, 2H, N—CH$_2$ proline), 4.07 (q, J=7.5 Hz, 2H, CH$_2$ ethyl ester), 4.33 (m, 1H, CH proline), 4.72 (m, 1H, CH alanine), 7.49 (d, J=5 Hz, 1H, ar C-5), 8.41 (s, 1H, ar C-3), 8.43 (d, J=5 Hz, 1H, ar C-6), 8.91 (br d, 1H, NH, disappears after shaking with D$_2$O), 10.66 (br s, 1H, NH acetylamino, disappears after shaking with D$_2$O). TLC(B): R$_f$=0.25

EXAMPLE 4

Synthesis of N-[(1,2-Dihydro-2-oxo-3-pyridinyl)carbonyl]-L-alanyl-L-proline ethyl ester (Compound No. 21)

To a stirred solution of 4.0 g (0.016 mol) of L-alanyl-L-proline ethyl ester hydrochloride and 8 ml triethylamine in 200 ml dioxane, maintained at room temperature, a suspension of 3.0 g (0.019 mol) 2-hydroxynicotinoyl chloride in 200 ml anhydrous dioxane is added dropwise over 1 hour. After stirring for a further 3 hours at room temperature, the solvent is distilled off under reduced pressure. The crude product thus obtained is dissolved in 500 ml of chloroform and the solution washed twice with 100 ml of 5% aqueous sodium carbonate. After drying the organic layer over anhydrous magnesium sulfate, the solvent is removed on a rotary evaporator. The solid crystallizes from methylene chloride/isopropyl ether to give 3.4 g of the title compound as a white microcrystalline solid (yield: 64%).

$^1$H-NMR (CDCl$_3$): 1.23 (t, J=7.2 Hz, 3H, CH$_3$ ethyl ester), 1.47 (d, J=6.8 Hz, 3H, CH$_3$ alanine), 2.10 (m, 4H, N—CH$_2$—CH$_2$—CH$_2$ proline), 3.70 (m, 2H, N—CH$_2$ proline), 4.18 (q, J=7.2 Hz, 2H, CH$_2$ ethyl ester), 4.50 (m, 1H, CH proline), 4.92 (m, 1H, CH alanine, converted to q, J=6.8 Hz, when shaking with D$_2$O), 6.44 (dd, J$_1$=7.4 Hz, J$_2$=6.2 Hz, 1H, ar C-5), 7.65 (dd, J$_1$=6.2 Hz, J$_2$=2.2 Hz, 1H, ar C-4), 8.48 (dd J$_1$=7.4 Hz, J$_2$=2.2 Hz, 1H, ar C-6), 10.20 (br d, 1H, amidic NH disappears when shaking with D$_2$O).

$^{13}$C-NMR (CDCl$_3$): 13.9 (CH$_3$ ethyl ester), 17.6 (CH$_3$ alanine), 24.7 (N—CH$_2$—CH$_2$ proline), 28.8 (N—CH$_2$—CH$_2$—CH$_2$ proline), 46.9 (N—CH$_2$ proline), 47.1 (CH alanine), 58.9 (CH proline), 61.0 (CH$_2$ ethyl ester), 107.4 (ar C-5), 120.9 (ar C-3), 138.9 (ar C-6), 145.1 (ar C-4), 163.0 (CO), 163.9 (CO), 171.7 (CO), 172.2 (CO). TLC(C): R$_f$=0.36

EXAMPLE 5

Synthesis of N-[(6-Chloro-3-pyridinyl)carbonyl]-L-alanyl-L-proline (Compound No. 22)

L-Alanyl-L-proline (1.0 g, 5.4 mmol) is dissolved in a mixture of 10.8 ml of 0.5 N potassium hydroxide and 750 mg (5.4 mmol) of anhydrous potassium carbonate, and 10 ml of acetonitrile are added. After cooling in an ice bath, a concentrated acetonitrile solution of 1.2 g of 6-chloronicotinoyl chloride is added dropwise while stirring and keeping the pH of the mixture at 12 to 13 with 1N potassium hydroxide, as necessary. Stirring is continued for 2 additional hours at room temperature, then the solution is neutralized to pH 6 with aqueous hydrochloric acid, and the solvent is distilled off under reduced pressure. The residue thus obtained is suspended in 50 ml of absolute ethanol, the remaining potassium chloride is separated by centrifugation, and the solvent of the clear solution is distilled off under reduced pressure. The crude product is purified through silica gel column chromatography, using absolute ethanol as eluant, to isolate 700 mg of the desired product (yield: 40%).

$^1$H-NMR (DMSO+D$_2$O): 1.26, 1–32 (two d, J=6.8 Hz, CH$_3$ alanine), 1.90 (m, 4H, N—CH$_2$—CH$_2$—CH$_2$ proline), 3.50 (m, 2H, N—CH$_2$ proline), 4.15 (m, 1H, CH proline), 4.70 (m, 1H, CH alanine), 7.62 (dd, J$_1$=8.2 Hz, J$_2$=3.0 Hz, 1H, ar C-5), 8.32 (dd, J$_1$=8.2 Hz, J$_2$=1 Hz, 1H, ar C-4), 8.87 (d, J=3.0 Hz, 1H, ar C-2).

$^{13}$C-NMR (DMSO+D$_2$O)*: 16.6, 18.1 (CH$_3$ alanine), 22.3, 24.7 (N—CH$_2$—CH$_2$ proline), 29.4, 31.7 (N—CH$_2$—CH$_2$—CH$_2$ proline), 46.8, 47.6, 47.7 (N—CH$_2$ proline and CH alanine), 61.1, 61.9 (CH proline), 124.8 (ar C-5), 129.6 (ar C-3), 139.6 (ar C-4), 149.9 (ar C-2), 153.4 (ar C-6), 164.5 (CO amidic bond pyridine ring-dipeptide), 171.2, 170.7 (CO peptide bend), 175.6 (COOH proline). TLC(E): R$_f$=0.54

Similarly, the following compound is prepared:

N-[(2-Ethoxy-3-pyridinyl)carbonyl]-L-alanyl-L-proline (Compound No. 23)

$^1$H-NMR (DMSO+D$_2$O) *: 1.26, 1.32 (two d, J=6.8 Hz, CH$_3$ alanine), 1.90 (m, 4H, N—CH$_2$—CH$_2$—CH$_2$ proline ), 3.50 (m, 2H, N—CH$_2$ proline ), 4.15, (m, 1H, CH proline ), 4.70 (m, 1H, CH alanine), 7.62 (dd, J$_1$=8.2 Hz, J$_2$=3.0 Hz, 1H, ar C-3), 8.32 (dd, J$_1$=8.2 Hz, J$_2$=1 Hz, 1H, ar C-4), 8.87 (d, J=3.0 Hz, 1H, ar C-6). TLC(D): R$_f$=0.35

EXAMPLE 6

Synthesis of N-[(6-Chloro-2-pyridinyl)carbonyl]-L-atanyl-L-proline (Compound No. 24)

A solution of 4.5 g (0.013 mol) of N-[(6-chloro-2-pyridinyl)carbonyl]-L-alanyl-L-proline ethyl ester (see example 1) in 42 ml of 1N ethanolic potassium hydroxide is stirred at room temperature for 3 hours. The resulting reaction mixture is diluted with 250 ml of absolute ethanol and neutralized with 6N ethanolic hydrochloric acid. The precipitate of potassium chloride thus formed is filtered, washed several times with absolute ethanol, and the solvent is eliminated under reduced pressure. The residue is purified by column chromatography over silica gel, using ethanol as eluant, to afford the title compound as a colourless solid (yield: 73%).

¹H-NMR (DMSO)*: 1.36, 1.32 (two d, J=6.8 Hz, CH₃ alanine), 2.10 (m, 4H, N—CH₂—CH₂—CH₂ proline), 3.65 (m, 2H, N—CH₂ proline), 4.30, (m, 1H, CH proline), 4.51, 4.75 (two m, 1H, CH alanine), 7.78 (dd, J₁=7.4 Hz, J₂=1.6 Hz, 1H, ar), 8.03 (dd, J₁=7.4 Hz, J₂=1.6 Hz, 1H, ar), 8.10 (dd, J₁=J₂=7.4 Hz, 1H, ar C-4), 8.70 (br d, 1H, amidic NH, disappears when shaking with D₂O).

¹³C-NMR (DMSO)*: 17.3, 18.6 (CH₃ alanine), 21.8, 24.6 (N—CH₂—CH₂ proline), 28.6, 30.8 (N—CH₂—CH₂—CH₂ proline), 46.3, 46.5, 46.7, 46.8 (N—CH₂ proline and CH alanine), 58.7, 59.3 (CH proline), 121.5 (C-3 ar), 127.8 (C-5 ar), 141.9 (C-4 ar), 149.6 (ar), 150.4 (ar), 161.8 (CO amidic bond pyridine ring-dipeptide), 170.3, 170.9 (CO peptidic bond), 173.5, 173.8 (COOH proline). TLC(E): R$_f$=0.55

*: Duplicity of signals is due to the presence of the isomers z-cis and z-trans through the peptidic linkage L-Ala-L-Pro.

By the same procedure, the following free acids are obtained from their corresponding esters:

N-[(2-chloro-3-pyridinyl)carbonyl]-L-alanyl-L-proline, (Compound No. 25), TLC(E): R$_f$=0.49

N-[(2-chloro-4-pyridinyl) carbonyl]-L-alanyl-L-proline, (Compound No. 26 ), TLC(E): R$_f$=0.55

N-[(1,2-dihydro-2-thioxo-4-pyridinyl) carbonyl]-L-alanyl-L-proline, (Compound No. 27), TLC(E): R$_f$=0.46

N-[(1,2-dihydro-2-thioxo-3-pyridinyl) carbonyl]-L-alanyl-L-proline, (Compound No. 28), TLC(E): R$_f$=0.45

N-[(1,6-dihydro-6-thioxo-3-pyridinyl) carbonyl]-L-alanyl-L-proline, (Compound No. 29), TLC(E): R$_f$=0.51

N-[(2-carboxy-6-pyridinyl) carbonyl]-L-alanyl-L-proline, (Compound No. 30), TLC(D) : R$_f$=0.29

N-[(2-carboxy-5-pyridinyl) carbonyl]-L-alanyl-L-proline, (Compound No. 31), TLC(D): R$_f$=0.25

N-[(2-carboxy- 3-pyridinyl) carbonyl]-L-alanyl-L-proline, (Compound No. 32), TLC(D): R$_f$=0.18

N-[(1,2-dihydro-2-oxo-4-pyridinyl) carbonyl]-L-alanyl-L-proline, (Compound No. 33), TLC(F): R$_f$=0.34

N-[(1,6-dihydro-6-oxo-2-pyridinyl) carbonyl]-L-alanyl-L-proline, (Compound No. 34), TLC(F): R$_f$=0.40

N-[(1,6-dihydro-6-oxo-3-pyridinyl) carbonyl]-L-alanyl-L-proline, (Compound No. 35), TLC(F): R$_f$=0.37

N-[(1,2-dihydro-2-oxo-3-pyridinyl) carbonyl]-L-alanyl-L-proline, (Compound No. 36), TLC(F): R$_f$=0.37

The structure of the mono- and diacids given above is confirmed by their spectroscopic data.

EXAMPLE 7

Pharmacological Results

A. Inhibition of Angiotensin I-Induced Contractions in Guinea-Pig Ileum

Segments of 1.5 cm of freshly excised and washed terminal ileum were suspended in 25-ml tissue baths containing Tyrode's solution at 31° C. and bubbled with 95% O₂-5% CO₂. With an initial load of 1.0 g, the resting tension after equilibration and the responses to Angiotensin I or Angiotensin II (both at 100 ng/ml) were monitored and recorded by means of an Ealing isometric transducer and a Lectromed polygraph. Several compounds of this invention were tested in this system, adding them to the bath 2 min. before the respective agonist.

At final bath concentrations of 10 ng/ml, the inhibitory effect of the tested compounds regarding the Angiotensin I-induced contractions was determined. The obtained results are given in Table I. All % inhibitions given therein are the average of results obtained with segments of ilea from 5 guinea-pigs. At final bath concentrations of 1 μg/ml none of the tested compounds produced an appreciable modification of the contractions induced by Angiotensin II.

TABLE I

| Compound No. | % Inhibition |
|---|---|
| 21 | 30.7 |
| 24 | 20.6 |
| 27 | 18.1 |
| 29 | 16.2 |
| 35 | 16.0 |
| Captopril | 28.9 |

B. Antihypertensive Activity in Spontaneously Hypertensive Rats (SHR)

In this recognized model of hypertension, male spontaneously hypertensive rats (315 to 376 g) with systolic blood pressures (SBP) >160 mm Hg were used. Systolic blood pressures were recorded on conscious animals by a tail cuff method (FS-40 blood pressure/pulse monitor). Prior to all measurements, the rats were placed in a restraining cylinder. Basal pressures were recorded and then the test compounds (including captopril as reference) were administered by the oral route at doses of 30 mg/kg (n=5/group). The pressures were monitored again 1, 2, 3, 4 and 24 h after administration of the test compounds. A control group (n=18) was included for comparison purposes.

Under the above conditions, compounds no. 8, 27 and 21 showed a significant antihypertensive effect. 1 h after administration, the average reduction of the SBPs was significantly different from the control group in the groups treated with compound no. 27 (28.4±3.16 mm Hg), compound no. 8 (32.6±7.49 mm Hg) and captopril (17.2±8.49 mm Hg). The reductions were also significantly different from the control after 2, 3, 4 and 24 h for compounds no. 8 and 27, whereas captopril was inactive after 24 h (Duncan-Kramer test, p<0.05). The mean basal SBPs (167.2 to 169.0 mm Hg) were not significantly different from that of the control (167.8±0.61 mm Hg).

Compound no. 21 at 30 mg/kg showed a significant reduction only after 2 h; at a dose of 45 mg/kg, the reductions were also significant after 2, 3, 4 and 24 h.

Antihypertensive effects were also observed in this model when compounds no. 8 and 27 were tested at oral doses of 7.5 and 15 mg/kg.

We claim:

1. A dipeptide derivative of formula (I)

$$(R_3)_n \diagup\!\!\diagup \text{—CONH—CH(R}_2\text{)—CON} \diagdown\!\!\diagdown \text{COR}_1 \quad (I)$$

(pyridine ring with N and R substituent, linked to —CONH—CH(R₂)—CON— and pyrrolidine ring with COR₁)

including tautomeric forms thereof, wherein:
n is 0 or 1;
R is OH, SH, NH₂, halogen, OR₄, SR₄, NHR₄ or N(R₄)₂, R₄ being selected from the group consisting of lower alkyl, phenyl, naphthyl, alkylcarbonyl having from 2 to 7 carbon atoms and benzoyl;

$R_1$ represents OH or lower alkoxy;

$R_2$ is lower alkyl;

$R_3$ represents halogen, $NO_2$, lower alkyl, or phenyl lower alkyl, or a pharmaceutically acceptable salt thereof.

2. The dipeptide derivative of claim 1, wherein R is OH, SH, Cl, $OR_4$, $SR_4$ or $NHR_4$, $R_4$ being selected from the group consisting of lower alkyl, phenyl, naphthyl and alkylcarbonyl groups having from 2 to 7 carbon atoms.

3. The dipeptide derivative of claim 1, wherein R is $OR_6$, $SR_6$, Cl or $NHR_7$, $R_6$ being selected from the group consisting of hydrogen, lower alkyl or phenyl; and $R_7$ is alkylcarbonyl having from 2 to 7 carbon atoms.

4. The dipeptide derivative of claim 3, wherein $R_6$ is hydrogen, methyl, ethyl or phenyl.

5. The dipeptide derivative of claim 1, wherein $R_1$ is OH or lower alkoxy.

6. The dipeptide derivative of claim 1, wherein $R_3$ is halogen.

7. A pharmaceutical composition comprising a pharmaceutically acceptable carrier and an effective amount of the dipeptide derivative of claim 1.

* * * * *